United States Patent
Fisher et al.

(10) Patent No.: US 10,582,982 B2
(45) Date of Patent: Mar. 10, 2020

(54) DISPOSABLE MULTI-PURPOSE TOOL FOR TOTAL KNEE ARTHROPLASTY

(71) Applicant: Zimmer, Inc., Warsaw, IN (US)

(72) Inventors: Michael G. Fisher, Reno, NV (US); Stephen M. Howell, Sacramento, CA (US)

(73) Assignee: Zimmer, Inc., Warsaw, IN (US)

( * ) Notice: Subject to any disclaimer, the term of this patent is extended or adjusted under 35 U.S.C. 154(b) by 542 days.

(21) Appl. No.: 15/073,167

(22) Filed: Mar. 17, 2016

(65) Prior Publication Data

US 2016/0278873 A1    Sep. 29, 2016

Related U.S. Application Data

(60) Provisional application No. 62/136,890, filed on Mar. 23, 2015.

(51) Int. Cl.
*A61F 2/46* (2006.01)
*A61B 90/00* (2016.01)
(Continued)

(52) U.S. Cl.
CPC ............ *A61B 90/06* (2016.02); *A61F 2/4657* (2013.01); *A61B 17/1764* (2013.01);
(Continued)

(58) Field of Classification Search
CPC . A61B 90/90; A61B 90/60; A61B 2002/4658; A61B 2002/4661;
(Continued)

(56) References Cited

U.S. PATENT DOCUMENTS 2,246,066 A * 6/1941 Rothe ............... G01B 3/18
                                                   33/427
4,769,040 A   9/1988 Wevers
(Continued)

FOREIGN PATENT DOCUMENTS

CN    203657640 U    6/2014
FR    3008605 A1    1/2015
(Continued)

OTHER PUBLICATIONS

"International Application Serial No. PCT US2016 052173, International Preliminary Report on Patentability dated Apr. 12, 2018", 8 pgs.
(Continued)

*Primary Examiner* — Matthew J Lawson
(74) *Attorney, Agent, or Firm* — Schwegman Lundberg & Woessner, P.A.

(57) ABSTRACT

A multi-purpose measurement tool comprises an elongate beam and a slide. The elongate beam extends from a first end to a second end, and comprises a first fixed jaw, a second fixed jaw, and a track. The first fixed jaw extends from the beam at the first end. The second fixed jaw extends from the beam opposite the first jaw and spaced from the first end. The track extends across the elongate beam through the first end. The slide has a first end extending from the track and a second end extending into the track. The slide has a moveable jaw extending from the slide opposite the first fixed jaw. The slide can also have a front face and a back face, each face with readable measurement indicia thereon.

19 Claims, 17 Drawing Sheets

(51) Int. Cl.
*A61F 2/38* (2006.01)
*A61B 17/17* (2006.01)

(52) U.S. Cl.
CPC ... *A61B 2090/036* (2016.02); *A61B 2090/061* (2016.02); *A61B 2562/0219* (2013.01); *A61F 2/38* (2013.01); *A61F 2002/4658* (2013.01); *A61F 2002/4668* (2013.01)

(58) Field of Classification Search
CPC ............ A61B 5/1075; A61B 2090/061; A61B 2090/068; A61F 2/4657; A61F 2002/4668
USPC .................... 606/102; 33/783, 784, 786, 810
See application file for complete search history.

(56) References Cited

U.S. PATENT DOCUMENTS

| | | | | |
|---|---|---|---|---|
| 5,084,982 | A | * | 2/1992 | Feng ...................... G01B 3/563 33/1 N |
| 5,133,760 | A | | 7/1992 | Petersen et al. |
| 5,519,942 | A | * | 5/1996 | Webb ....................... G01C 9/28 33/281 |
| 5,722,179 | A | * | 3/1998 | Zanier ...................... G01B 3/20 33/810 |
| 6,096,082 | A | | 8/2000 | Stegmuller et al. |
| 6,421,927 | B1 | * | 7/2002 | Bach ......................... G01B 3/02 33/427 |
| 7,691,150 | B2 | | 4/2010 | Cronin et al. |
| 8,603,101 | B2 | | 12/2013 | Claypool et al. |
| 9,003,672 | B2 | * | 4/2015 | Lozano, IV ............ F24S 25/33 33/809 |
| 10,130,375 | B2 | | 11/2018 | Yager et al. |
| 10,136,997 | B2 | | 11/2018 | Yager |
| 2004/0204766 | A1 | | 10/2004 | Siebel |
| 2006/0142774 | A1 | | 6/2006 | Metzger |
| 2006/0200163 | A1 | | 9/2006 | Roger et al. |
| 2006/0241634 | A1 | | 10/2006 | Tuttle et al. |
| 2008/0184582 | A1 | * | 8/2008 | Kim ........................ G01B 3/205 33/784 |
| 2009/0149963 | A1 | | 6/2009 | Sekel |
| 2010/0249657 | A1 | * | 9/2010 | Nycz ..................... A61F 2/4609 600/587 |
| 2010/0293802 | A1 | * | 11/2010 | Stockman .............. G01B 3/205 33/784 |
| 2011/0029091 | A1 | | 2/2011 | Bojarski et al. |
| 2011/0099829 | A1 | * | 5/2011 | Prior ........................ G01B 3/20 33/810 |
| 2012/0330319 | A1 | * | 12/2012 | Birkbeck .............. A61F 2/4609 606/91 |
| 2013/0024001 | A1 | | 1/2013 | Wentorf et al. |
| 2013/0218284 | A1 | | 8/2013 | Eickmann et al. |
| 2013/0227854 | A1 | * | 9/2013 | Zhang ................... G01B 3/002 33/809 |
| 2014/0025081 | A1 | | 1/2014 | Lorio et al. |
| 2014/0228851 | A1 | | 8/2014 | Guloy, Jr. et al. |
| 2015/0045801 | A1 | | 2/2015 | Axelson, Jr. et al. |
| 2015/0196366 | A1 | * | 7/2015 | Kim ..................... A61B 17/155 606/102 |
| 2016/0030053 | A1 | | 2/2016 | Yager et al. |
| 2017/0086982 | A1 | | 3/2017 | Yager |
| 2019/0046215 | A1 | | 2/2019 | Yager et al. |
| 2019/0046323 | A1 | | 2/2019 | Yager |

FOREIGN PATENT DOCUMENTS

| | | |
|---|---|---|
| WO | WO-2004084740 A1 | 10/2004 |
| WO | WO-2007053905 A1 | 5/2007 |
| WO | WO-2016153927 A1 | 9/2016 |
| WO | WO-2017058535 A1 | 4/2017 |

OTHER PUBLICATIONS

"U.S. Appl. No. 14/809,810, Final Office Action dated May 2, 2018", 10 pgs.
"U.S. Appl. No. 15/267,826, Response filed Feb. 22, 2018 to Restriction Requirement dated Dec. 27, 2017", 6 pgs.
"U.S. Appl. No. 14/525,595, filed Oct. 28, 2014", 40 pgs.
"U.S. Appl. No. 14/809,810, filed Jun. 15, 2018 to Final Office Action dated May 2, 2018", 14 pgs.
U.S. Appl. No. 14/809,810, Advisory Action dated Jun. 27, 2018, 3 pgs.
"U.S. Appl. No. 14/809,810, Corrected Notice of Allowability dated Aug. 30, 2018", 2 pgs.
"U.S. Appl. No. 15/267,826, Notice of Allowability dated Aug. 31, 2018", 2 pgs.
"U.S. Appl. No. 14/809,810, Non Final Office Action dated Sep. 29, 2017", 9 pgs.
"U.S. Appl. No. 14/809,810, filed Dec. 27, 2017 to Non Final Office Action dated Sep. 29, 2017", 14 pgs.
"U.S. Appl. No. 15/267,826, Restriction Requirement dated Dec. 27, 2017", 6 pgs.
"International Application Serial No. PCT/US2016/022907, International Preliminary Report on Patentability dated Oct. 5, 2017", 9 pgs.
"International Application Serial No. PCT/US2016/022907, International Search Report dated Jul. 7, 2016", 7 pgs.
"International Application Serial No. PCT/US2016/022907, Written Opinion dated Jul. 7, 2016", 13 pgs.
"International Application Serial No. PCT/US2016/052173, International Search Report dated Jan. 10, 2017", 6 pgs.
"International Application Serial No. PCT/US2016/052173, Written Opinion dated Jan. 10, 2017", 7 pgs.
"Natural-Knee® Modular Cemented Baseplate", [Online] retrieved from the internet:URL:http://www.zimmer.com/content/dam/zimmer-web/documents/en-US/pdf/medical-professionals/knee/natural-knee-modular-cemented-baseplate-brochure.pdf, (2004), 4 pgs.
"U.S. Appl. No. 15/267,826, Non Final Office Action dated Apr. 5, 2018", 8 pgs.
"U.S. Appl. No. 15/267,826, filed Jun. 26, 2018 to Non Final Office Action dated Apr. 5, 2018", 9 pgs.
"U.S. Appl. No. 14/809,810, Notice of Allowance dated Aug. 15, 2018", 7 pgs.
"U.S. Appl. No. 15/267,826, Notice of Allowance dated Aug. 15, 2018", 7 pgs.
U.S. Appl. No. 16/162,520, filed Nov. 14, 2018, 6 pgs.
U.S. Appl. No. 16/162,530, filed Nov. 14, 2018, 5 pgs.
"U.S. Appl. No. 16/162,530, Non Final Office Action dated Sep. 16, 2019", 8 pages.

* cited by examiner

DISPOSABLE MULTI-PURPOSE TOOL FOR TOTAL KNEE ARTHROPLASTY

CLAIM OF PRIORITY

This application claims the benefit of U.S. Provisional Patent Application Ser. No. 62/136,890, filed on Mar. 23, 2015, the benefit of priority of which is claimed hereby, and which is incorporated by reference herein in its entirety.

FIELD

The present subject matter relates to orthopedic prostheses, and, more particularly, to systems and methods for performing total knee anthroplasties.

BACKGROUND

Orthopedic prostheses are commonly utilized to repair and/or replace damaged bone and tissue in the human body. For example, a knee prosthesis can be used to restore natural knee function by repairing damaged or diseased articular surfaces of the femur and/or tibia. Knee prostheses can include a femoral component implanted on the distal end of the femur, which articulates with a tibial component implanted on the proximal end of a tibia to replicate the function of a healthy natural knee.

Osteoarthritis, a degenerative joint disease initiated through the loss of articular cartilage, can necessitate a knee replacement. A number of causes, including hereditary, lifestyle, mechanical deficits, and others, can lead to osteoarthritis. Knee prostheses can be used to restore the knee to the natural or anatomical alignment, including restoring natural constitutional varus, or to mechanical alignment where the yarns or valgus is corrected, referencing the long axis of the tibia, often including a series of soft-tissue manipulations.

The present inventors recognize, among other things, an opportunity for improved patient satisfaction following a total knee arthroplasty (TKA) through the use of a kinematically aligned TKA and surgical instruments to aid in the procedure. In particular, the inventors recognize the importance of improving the accuracy and repeatability of the steps in a TKA procedure in order to, among other things, improve patient comfort and functionality.

The knee is a complex joint, and accurate placement of the prosthetic knee components is one of several goals of knee replacement surgery. Recently, prosthetic knee implant systems have been introduced with additional sizes in efforts to more closely match the wide variety of patient sizes. The additional size options increases the need for even more accurate placement of the prosthetic components. Having additional prosthetic component sizes, with smaller shifts between those sizes can only be best appreciated with more accurate placement. In addition, accurate placement of the components relative to patient-specific anatomical origins has been reported to lead to improved patient function and satisfaction. Accordingly, in efforts to improve patient satisfaction after total knee replacement surgery, and consistent with the latest prosthetic component designs and additional sizes offered, there is a need for accurate, repeatable, easy to use, cost-effective, multi-functional instruments and surgical methods.

To further illustrate the systems and methods disclosed herein, following non-limiting examples are provided:

Example 1, a multi-purpose measurement tool comprises: an elongate beam extending from a first end to a second end, the elongate beam comprising a first fixed jaw extending from the beam at the first end; a second fixed jaw extending from the beam opposite the first jaw and spaced from the first end; and a track extending across the elongate beam through the first end; and a slide having a first end extending from the track and a second end extending into the track, the slide having a moveable jaw extending from the slide opposite the first fixed jaw; and the slide having a front face and a back face, each face with readable measurement indicia thereon.

Example 2 can include, or can optionally be combined with the subject matter of Example 1, to optionally include an elongate beam comprising a plate portion; a first rail extending from the plate portion to define a first side of the track and a portion of the first fixed jaw; and a second rail extending from the plate portion to define a second side of the track and a portion of the second fixed jaw; wherein the slide with the moveable jaw slides in the track defined by the first rail and second rail of the plate portion; and wherein the plate portion, the first rail and the second rail define an outer perimeter of the elongate beam.

Example 3 can include, or can optionally be combined with the subject matter of Examples 1 or 2, to optionally include a track extending along a major axis of the beam and the jaws extend transverse to the major axis.

Example 4 can include, or can optionally be combined with the subject matter of Examples 1, 2 or 3, to optionally include a plate portion that is transparent.

Example 5 can include, or can optionally be combined with the subject matter of Examples 1, 2, 3 or 4, to optionally include a slide including first indicia indicating a scale on a first side in a first orientation; and second indicia indicating the scale on a second side in a second orientation opposite the first orientation.

Example 6 can include, or can optionally be combined with the subject matter of Examples 1, 2, 3, 4 or 5, to optionally include a second fixed jaw that is spaced from the first end a distance equal to a width of the moveable jaw.

Example 7 can include, or can optionally be combined with the subject matter of Examples 1, 2, 3, 4, 5 or 6, to optionally include a second end of the elongate beam includes a level indicator.

Example 8 can include, or can optionally be combined with the subject matter of Examples 1, 2, 3, 4, 5, 6 or 7, to optionally include a level indicator comprising a bubble.

Example 9 can include, or can optionally be combined with the subject matter of Examples 1, 2, 3, 4, 5, 6, 7 or 8, to optionally include a level indicator being is selected from the group consisting of a roller ball, a plumb bob, or an accelerometer-based level indicator.

Example 10 can include, or can optionally be combined with the subject matter of Examples 1, 2, 3, 4, 5, 6, 7, 8 or 9, to optionally include a level indicator that indicates a level reading when the elongate beam is disposed at forty-five degrees from horizontal.

Example 11 can include, or can optionally be combined with the subject matter of Examples 1, 2, 3, 4, 5, 6, 7, 8, 9 or 10, to optionally include an attachment including the level indicator.

Example 12 can include, or can optionally be combined with the subject matter of Examples 1, 3, 4, 5, 6, 7, 8, 9, 10 or 11, to optionally include a second end of the elongate beam that is configured to receive the attachment and includes a connection to immobilize the attachment.

Example 13 can include, or can optionally be combined with the subject matter of Examples 1, 2, 3, 4, 5, 6, 7, 89, 10, 11 or 12, to optionally include a first fixed jaw and moveable jaw that comprise a thickness gauge.

Example 14 can include, or can optionally be combined with the subject matter of Examples 1, 2, 3, 4, 5, 6, 7, 8, 9, 10, 11, 12 or 13, to optionally include a second fixed jaw and first end of the elongate beam that comprise a depth gauge.

Example 15 can include, or can optionally be combined with the subject matter of Examples 1, 2, 3, 4, 5, 6, 7, 8, 9, 10, 11, 12, 13 or 14, to optionally include a slide that includes a thumb grip.

Example 16 can include, or can optionally be combined with the subject matter of Examples 1, 2, 3, 4, 5, 6, 7, 8, 9, 10, 11, 12, 13, 14 or 15, to optionally include a first side of the elongate beam from which the first fixed jaw extends includes a fixation device for immobilizing the slide relative to the elongate beam.

Example 17 can include, or can optionally be combined with the subject matter of Examples 1, 2, 3, 4, 5, 6, 7, 8, 9, 10, 11, 12, 13, 14, 15 or 16, to optionally include a second side of the elongate beam that includes ergonomic grips.

In Example 18, a method of using a multi-purpose measurement tool during a total knee arthroplasty comprises: measuring a natural anterior-posterior offset of a tibia from a femur using a second side of a tool; measuring distal femoral resections using a first side of the tool; measuring posterior femoral resections using the first side of the tool; and measuring an anterior-posterior offset of an implanted prosthetic tibia from an implanted prosthetic femur using the second side of the tool.

Example 19 can include, or can optionally be combined with the subject matter of Example 18, to optionally include using a level device attached to the tool to evaluate an angular relationship between the femur and tibia; and measuring the natural and implanted anterior-posterior offsets when the femur and tibia are disposed at a predetermined angular relationship to each other as indicated by the level device.

Example 20 can include, or can optionally be combined with the subject matter of Examples 18 or 19, to optionally include a predetermined angular relationship that is ninety degrees to each other.

Example 21 can include, or can optionally be combined with the subject matter of Examples 18, 19 or 20, to optionally include separating a level device attached to the tool from the tool; placing the level device in engagement with a drill guide; using the level device to evaluate an angular relationship between the femur and tibia; and drilling a hole in the femur using a drill engaged with the drill guide when the femur and tibia are disposed at a predetermined angular relationship to each other as indicated by the level device.

Example 22 can include, or can optionally be combined with the subject matter of Examples 18, 19, 20 or 21, to optionally include a predetermined angular relationship that is 90 degrees to each other.

Example 23 can include, or can optionally be combined with the subject matter of Examples 18, 19, 20, 21 or 22, to optionally include the natural and implanted anterior-posterior offsets of tibia from the femur are measured using a sliding depth gauge extending from a first end of the tool.

Example 24 can include, or can optionally be combined with the subject matter of Examples 18, 19, 20, 21, 22 or 23, to optionally include the distal and posterior femoral resections are measured using a sliding thickness gauge extending from the first end of the tool.

Example 25, a system for performing a total knee arthroplasty comprises: a multi-function tool including a depth gauge for measuring an anterior-posterior offset between a tibia and a femur; a level indicator attached to the multi-function tool for providing an indication of an angular relationship between the tibia and femur while measuring the anterior-posterior offset; and a drill guide for aligning a drill bit with the tibia or the femur; wherein the level indicator is separable from the multi-function tool and mountable to the drill guide.

Example 26 can include, or can optionally be combined with the subject matter of Example 25, to optionally include a thickness gauge and the depth gauge.

Example 27 can include, or can optionally be combined with the subject matter of Examples 25 or 26, to optionally include a thickness gauge and a depth gauge that share a common slide.

Example 28 can include, or can optionally be combined with the subject matter of Examples 25, 26 or 27, to optionally include a level indicator that provides an indication of an angular relationship between the tibia and femur while using the drill guide.

Example 29 can include, or can optionally be combined with the subject matter of Examples 25, 26, 27 or 28, to optionally include a drill guide comprising a stabilizer configured to lay across the tibia or the femur; a drill bit sleeve extending from the stabilizer and configured to guide a drill bit; and a handle extending from the drill bit sleeve.

Example 30 can include, or can optionally be combined with the subject matter of Examples 25, 26, 27, 28 or 29, to optionally include a stabilizer including a feature for engaging a feature of the level indicator such that the level indicator can be removably attached to the stabilizer.

Example 31 can include, or can optionally be combined with the subject matter of Examples 25, 26, 27, 28, 29 or 30, to optionally include the multi-function tool and the level indicator include engagement features for removably attaching the level indicator to the multi-function tool.

Example 32 can include, or can optionally be combined with the subject matter of Examples 25, 26, 27, 28, 29, 30 or 31, to optionally include a level indicator including a body comprising a first edge upon which a level indicator device is disposed; a second edge for mating with the stabilizer; and a third edge for mating with the multi-function tool.

Example 33 can include, or can optionally be combined with the subject matter of Examples 25, 26, 27, 28, 29, 30, 31 or 32, to optionally include a first edge that is disposed at forty-five degrees to both the second edge and the third edge.

In Example 34, the system or method of any one or any combination of Examples 1-33 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

It has been established that a kinematically aligned total knee arthroplasty (TKA) can improve the results of the TKA, including overall patient satisfaction and mobility. A primary goal of kinematically aligned TKA is to position the femoral and tibial components of a knee prosthesis such that the angles and levels of the distal and posterior femoral joint lines and the tibial joint line are restored to the natural or constitutional alignment of the patient prior to the patient having developed osteoarthritis. The kinematically aligned TKA can include a determination of three kinematic axes. The multi-purpose tools described herein may be used to facilitate alignment of one or more of these axes with each other or tools of the TKA procedure.

Figure 1:
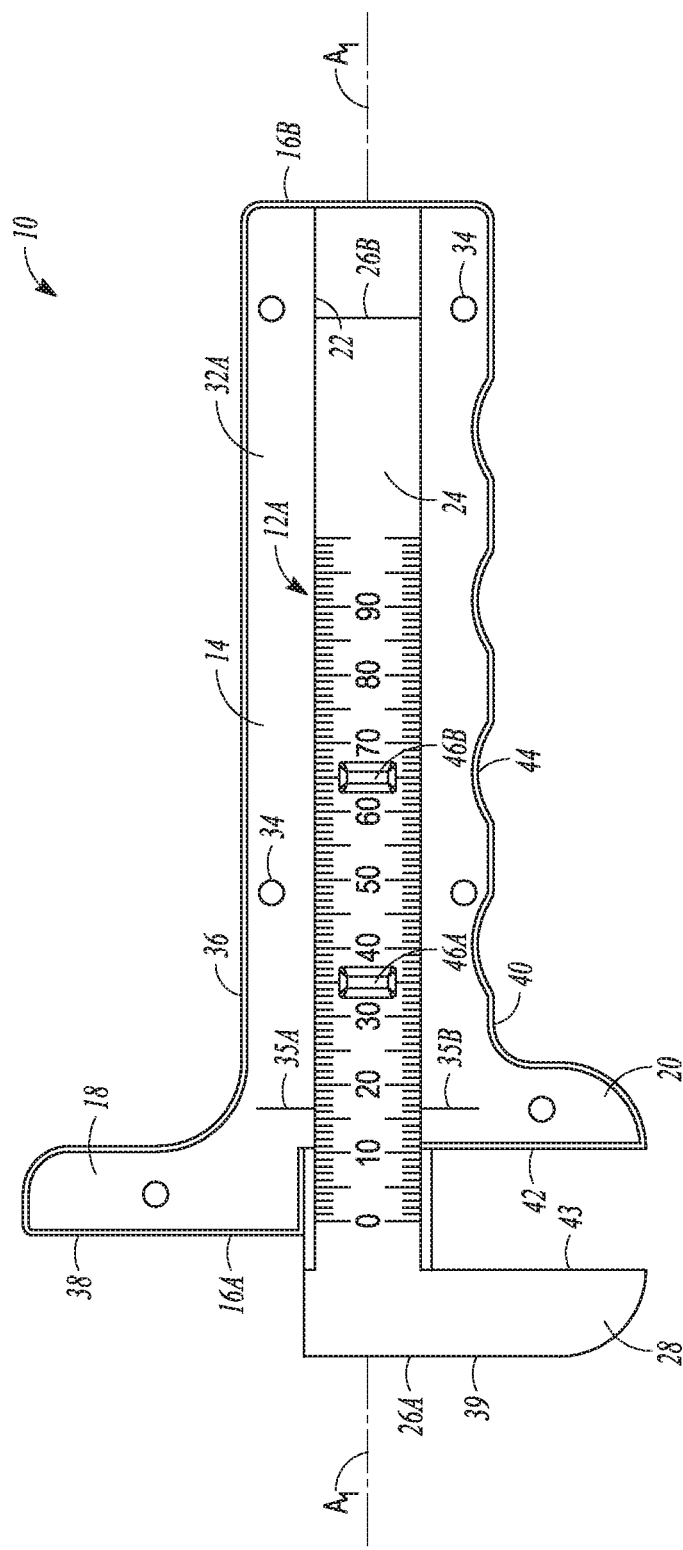
FIG. 1 is a perspective view of a first side of a multi-purpose tool having a thickness gauge and a depth gauge that utilize a common scale indicated on a slide.
Figure 2:
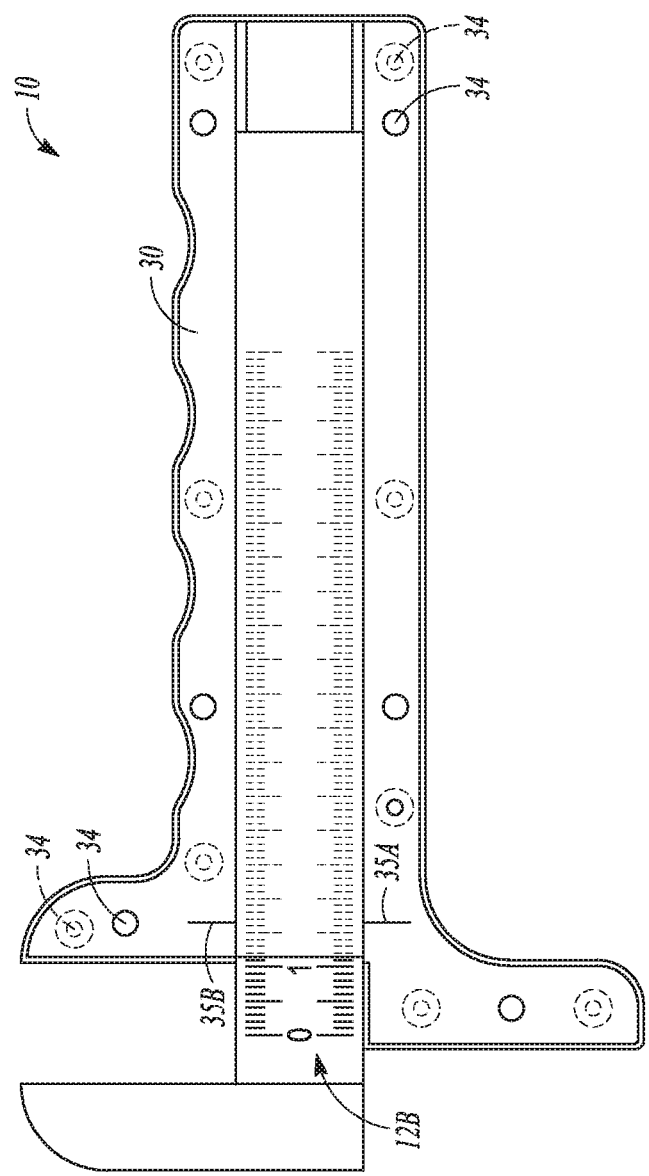
FIG. 2 is a perspective view of a second side of the multi-purpose tool of FIG. 1 showing the common scale reproduced upside down with respect to the first side on the slide.

FIG. 1 is a perspective view of a first side of multi-purpose tool 10 having a thickness gauge and a depth gauge that utilize first scale 12A readable in a first orientation. FIG. 2 is a perspective view of a second side of multi-purpose tool 10 of FIG. 1 showing second scale 12B readable in a second orientation opposite that of the first orientation. As shown in FIGS. 1 and 2, and FIGS. 3B and 3C, indicia can be provided in opposite orientations with respect to horizontal (FIGS. 1 and 2) or vertical (FIGS. 3B and 3C) lettering.

Tool 10 can include beam 14 that extends between first end 16A and second end 16B, first fixed jaw 18, second fixed jaw 20, track 22, and slide 24—which extends between first end 26A and 26B—that includes moveable jaw 28. First fixed jaw 18 and moveable jaw 28 can be configured as a depth gauge, while second fixed jaw 20 and moveable jaw 28 can be configured as thickness gauge or caliper.

As will be discussed in greater detail below, tool 10 can be used in kinematically-aligned total knee arthroplasty procedures, as are discussed in U.S. provisional patent application No. 62/031,572, which is hereby is incorporated by reference in its entirety. Such procedures involve measuring the anterior-posterior offset of the tibia from the femur of the natural knee and the replacement knee, measuring the thicknesses of resections removed from distal and posterior portions of the femur, as well as ensuring that these steps and other steps are carried out while the patient and equipment are in the proper orientation and are properly aligned. The multi-function, multi-purpose tool of the present disclosure can be configured to carry out all or some of these measurements while in the proper orientation, as well to facilitate other steps of the procedure to be properly carried out.

In one example, beam 14 can be comprised of a polymer or plastic material. In one example, beam 14 is comprised of an inexpensive material so as to be disposable. However, beam 14 can be comprised of other materials such as metals and can be reusable. As shown in FIG. 2, beam 14 can include plate 30, which has an outer perimeter matching that of beam 14. As shown in FIG. 1, rails 32A and 32B can be mounted on beam 14 to form track 22. Rails 32A and 32B can be attached with connection features 34, which can comprise rivets, snap-fit connectors or any suitable connector, or combinations thereof. Plate 30 can be transparent so that scale 12B is visible through plate 30 when fully inserted into track 22. In other examples, such as shown in FIGS. 3A-3E, rails 32A and 32B can be formed integrally with plate 30 so that beam 14 comprises one single component. In such an embodiment, the entirety of beam 14 can be transparent.

Track 22 extends along axis $A_1$ within beam 14 so that slide 24 can extend axially from beam 14. First fixed jaw 18 can extend from side 36 of beam 14 at first end 16A. Surface 38 of first fixed jaw 18 can be perpendicular to axis $A_1$ and slide 24 so that hash marks of scales 12A and 12B can align with surface 38, e.g. when slide 24 is extended from track 22. In one example, the hash marks provide an indication of how far surface 39 is spaced from surface 38 on axis $A_1$, thereby providing a depth gauge. Additionally, beam 14 can be provided with hash mark 35A, or an arrow, along track 22 to indicate the distance slide 24 has been extended.

Second fixed jaw 20 can extend from side 40 of beam 14 spaced from first end 16A. Surface 42 of second fixed jaw 20 can be perpendicular to axis $A_1$ and slide 24 so that hash marks of scales 12A and 12B align with surface 42, e.g. when slide 24 is extended from track 22. In one example, the hash marks provide an indication of how far surface 43 is spaced from surface 42 on axis $A_1$, thereby providing a thickness gauge or caliper. Additionally, beam 14 can be provided with hash mark 35B, or an arrow, along track 22 to indicate the distance slide 24 has been extended.

Tool 10 can also include other features to facilitate handling and manipulation of the device. For example, beam 14 can include ergonomic contouring 44 to facilitate gripping of tool 10 with fingers. Also, slide 24 can include thumb grips 46A and 46B to facilitate extension and retraction of moveable jaw 28.

Figure 3A:
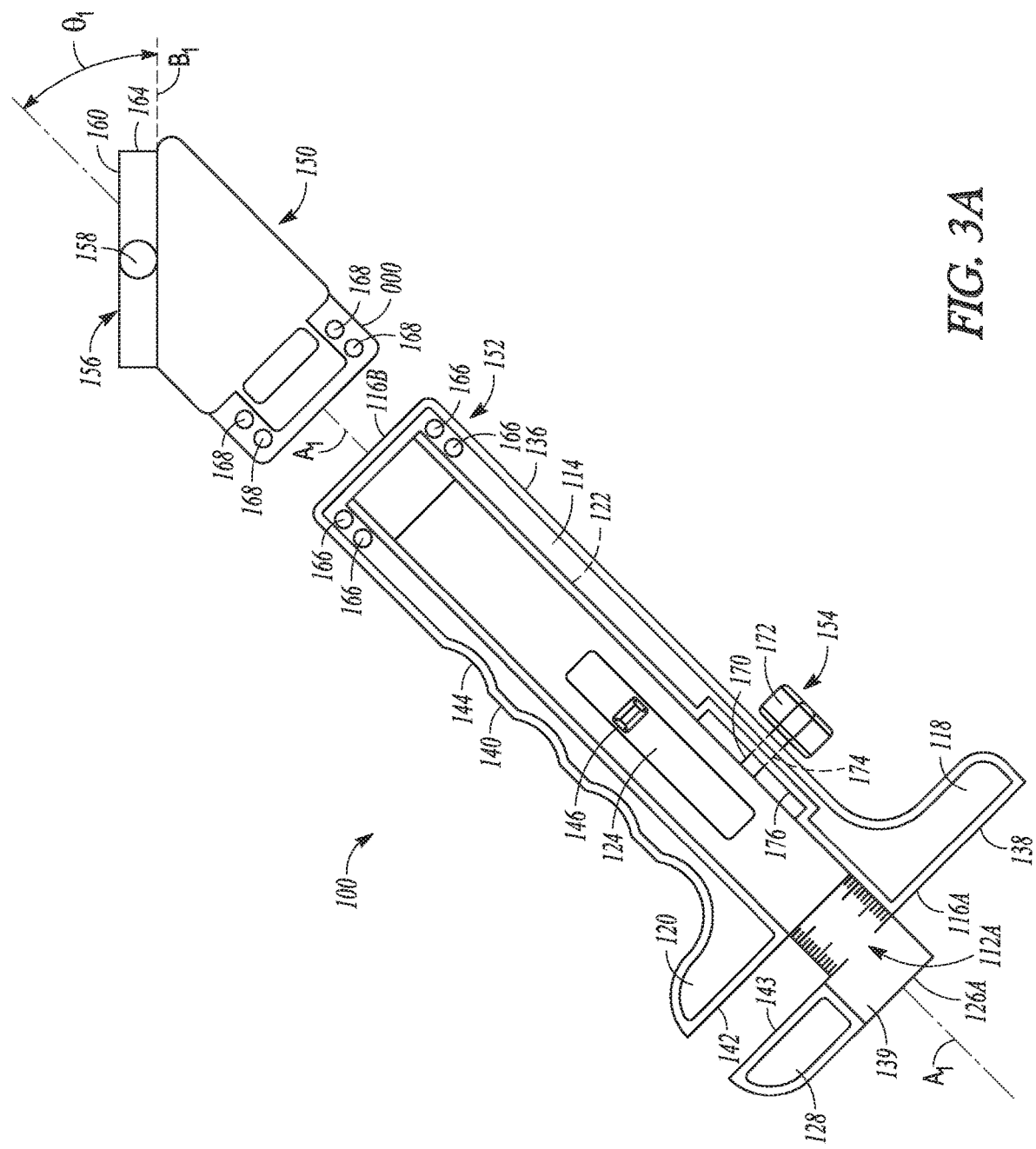
FIG. 3A is an exploded view of another example of a multi-purpose tool having a separable piece including a roller ball level indicator.
Figure 3B:
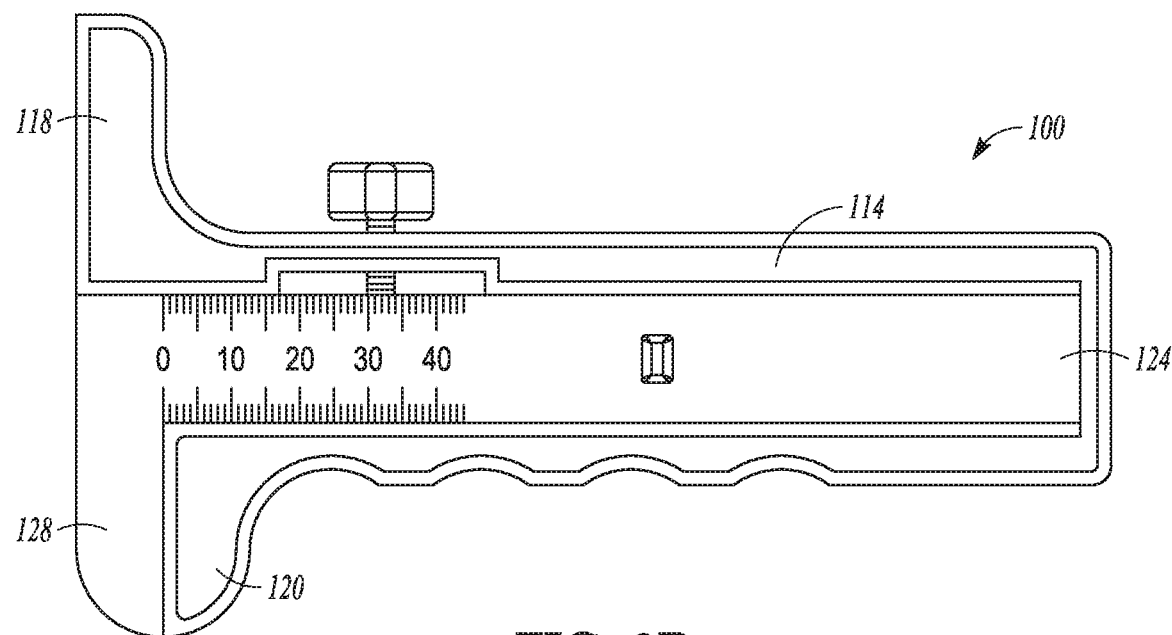
FIGS. 3B and 3C show additional views of the multi-purpose tool of FIG. 3A.
Figure 3C:
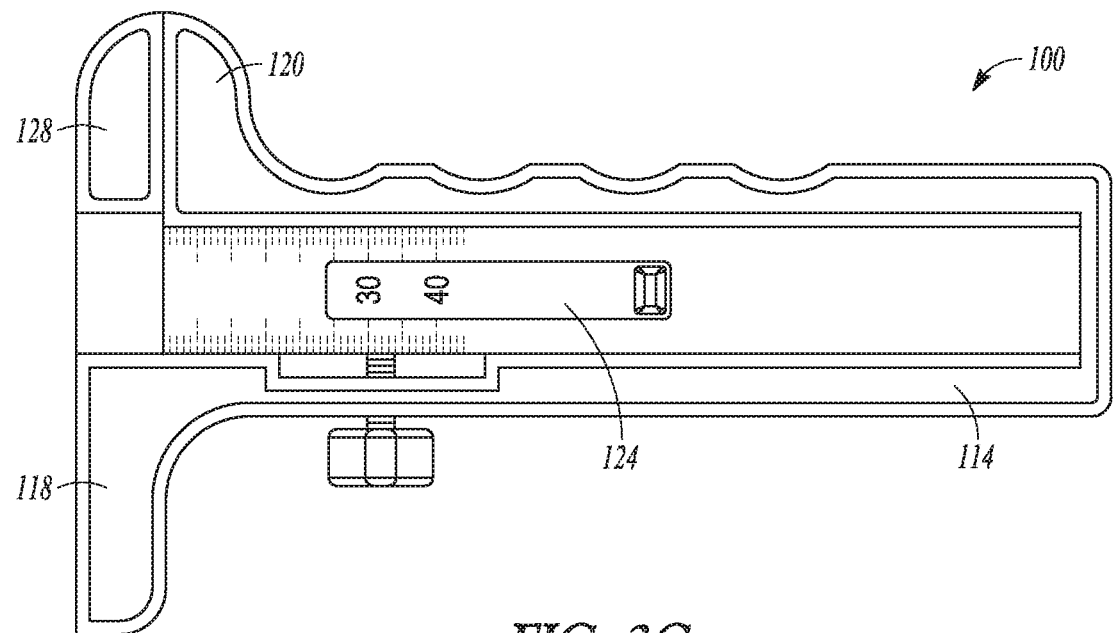

FIG. 3A is an exploded view of another example of multi-purpose tool 100 having separable piece 150 including a roller ball level indicator. FIGS. 3B and 3C show additional views of tool 10 from FIG. 3A. Tool 100 can include many of the same features of tool 10 of FIGS. 1 and 2 and such features are denoted with similar reference numerals, but in the one-hundred series. Tool 100 can be different from tool 10 in that tool 100 1) includes attachment features 152 for connecting with separable piece 150, 2) includes fixation feature 154 for immobilizing slide 124, and 3) does not include connection features 34 because beam 114 is a single piece.

Figure 4A:
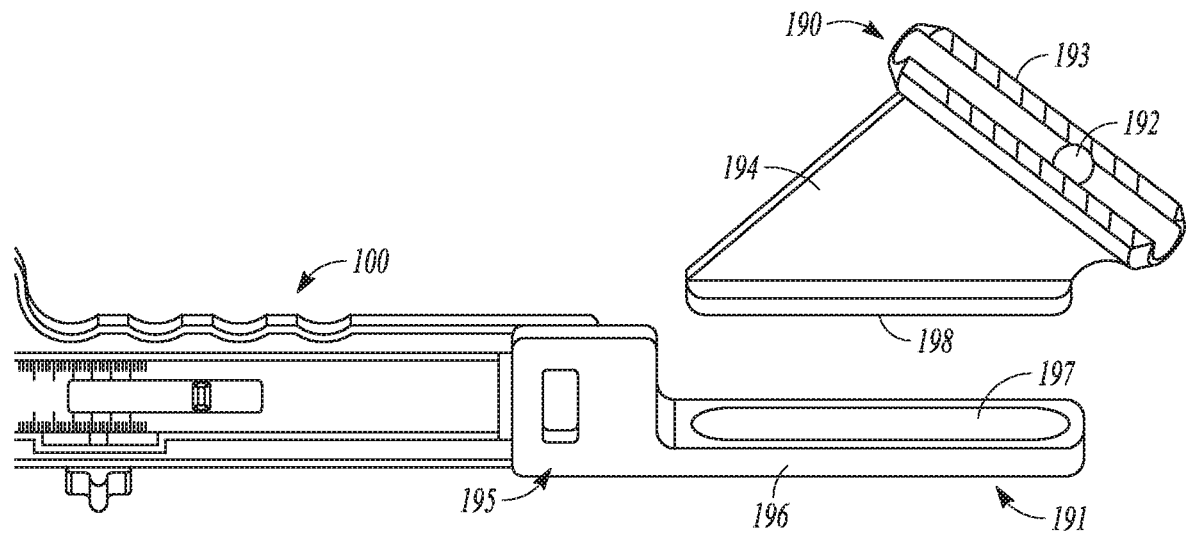
FIG. 4A is a perspective view of a level indicator being removed from a separable piece attached to a multi-purpose tool.
Figure 5A:
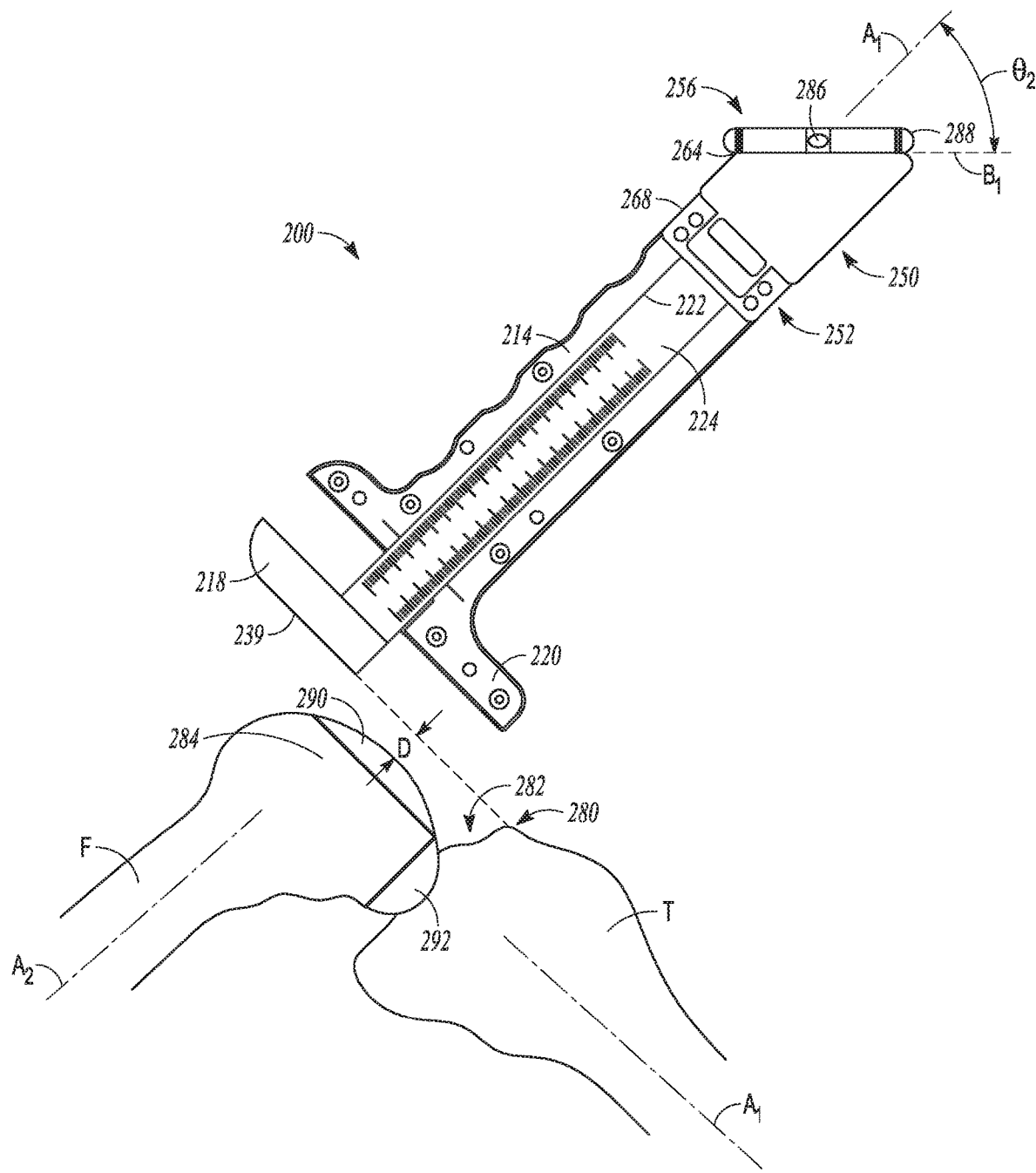
FIG. 5A is a perspective view of another example of a multi-purpose tool having a separable piece including a bubble level indicator oriented to measure an anterior-posterior offset of the anterior portion of a tibia to the distal end of a femur.

Separable piece 150 can include level device 156, which in the example of FIG. 3A, comprises roller ball 158 disposed in track 160, and coupler 162 which can be configured to join with fixation features 152 of beam 114. In other examples, a level device may comprise a bubble level as shown in FIGS. 4A, 5A and 6B. Separable piece 150 can have a triangular shape such that surface 164 extends along axis $B_1$ at angle $\theta_1$ of forty-five degrees from axis $A_1$. As such, roller ball 158 will center in track 160—indicating a level reading—when axis $A_1$ is forty-five degrees, e.g. forty-five degrees to the horizon (i.e. horizontal).

Attachment features 152 of beam 114 can comprise recesses 166, such as holes through beam 114 or blind-end bores within beam 114, that mate with protrusions 168 on separable piece 150. As such, separable piece 150 can slide into or over beam 114 to form a detent mechanism that immobilizes separable piece relative to beam 114. In another example, such as that shown in FIG. 4A, the separable piece may be attached to the tool using a clip device.

Fixation feature 154 can comprise a screw mechanism having threaded shaft 170 and head 172. Threaded shaft 170 can extend through bore 174 in beam 114 and into recess 176 on track 122. As such, head 172 can be rotated to advance shaft 170 into bore 174 to engage slide 124 to prevent slide 124 from moving within track 122.

Figure 3D:
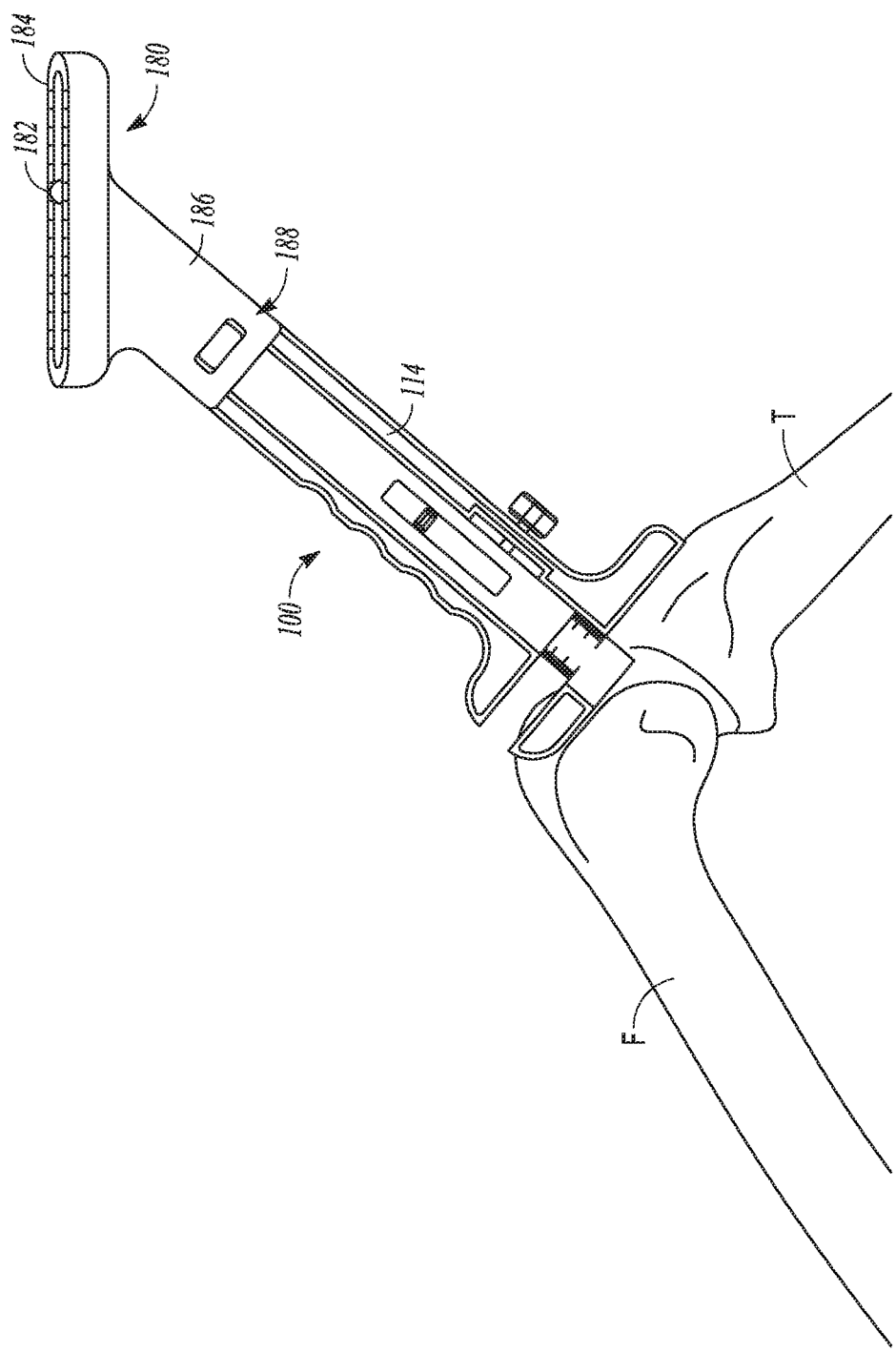
FIG. 3D shows another example of the multi-purpose tool of FIGS. 3B and 3C having a ball-in-track level indicator similar to the one shown in FIG. 3A.

FIG. 3D shows another example of multi-purpose tool 100 having a roller ball level indicator similar to the one shown in FIG. 3A. FIG. 3D shows a ball-in-track level indicator 180 in which roller ball 182 is disposed in track 184 formed in separable piece 186. The body of separable piece 186 includes hash marks along track 184 in order for a user of level indicator 180 to gain an understanding of the orientation of tool 100. The body of separable piece 186 also includes clip 188 for attaching to beam 114 with a mating feature. Level indicator 180 is disposed on separable piece 186 relative to tool 100 to indicate "level" when femur F is disposed at ninety degrees to tibia T in the supine position while taking an anterior-posterior (A-P) measurement, as discussed in greater detail below.

Figure 3E:
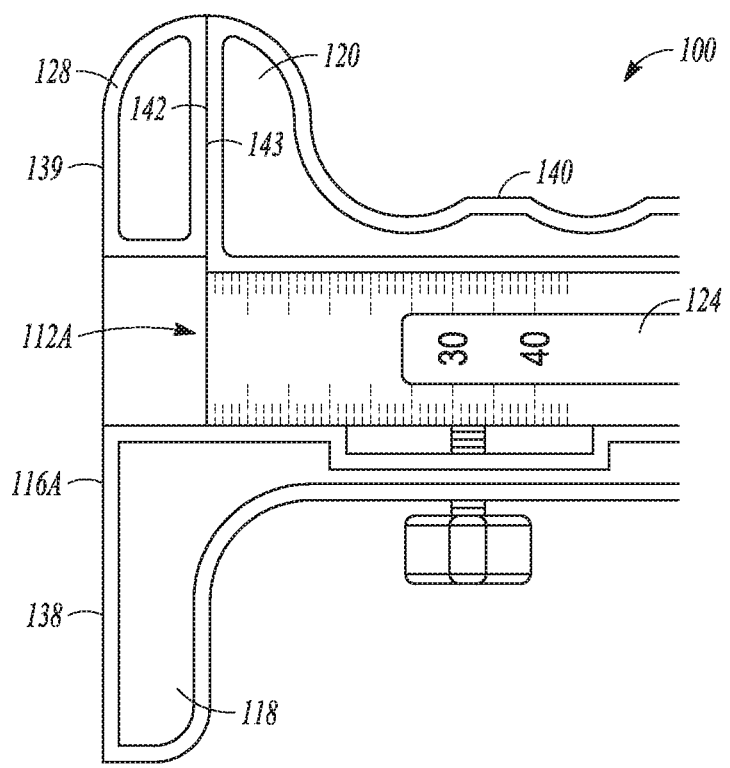
FIG. 3E is a perspective view of a distal measurement end of the multi-purpose tool of FIG. 3A showing a moveable jaw engaged with a fixed jaw of the thickness gauge.

FIG. 3E is a perspective view of distal measurement end 116A of multi-purpose tool 100 of FIG. 3A showing moveable jaw 128 engaged with fixed jaw 120. Disposed as such, surface 142 of fixed jaw 120 is engaged flush with surface 143 of moveable jaw 128. Also, the width of moveable jaw 128 can approximately equal the distance that fixed jaw 120 is spaced from first end 116A of beam 114 such that when slide 124 is fully retracted into track 122, surface 138 of fixed jaw 118 aligns with surface 139 of moveable jaw 128. Also in this position, the zero ("0") hash mark of the indicia of scale 112A is aligned with surface 142. Thus, the movement of surface 139 away from surface 138 along axis $A_1$ provides a depth gauge, with measurements being read on scale 112A at surface 142 for the distance that surface 139 is away from surface 138. Also, the movement of surface 143 away from surface 142 along axis $A_1$ provides a thickness gauge, or caliper, with measurements also being read on scale 112A at surface 142 for the distance between surfaces 143 and 142.

FIG. 4A is a perspective view of level indicator 190 being removed from separable piece 191 attached to multi-purpose tool 100. In the shown example, level indicator 190 comprises bubble level in which bubble 192 moves within tube 193 mounted on body 194, similarly to the functionality of the device described with reference to FIG. 5A, below. Separable piece 191 includes clip 195 and tray 196. Tray 196 can be configured to have slot 197 that receives mating key 198 on body 194. Slot 197 and key 198 are configured so that level indicator 190 can be repeatedly attached and separated from separable piece 191. In one example, a force fit or interference fit is provided between slot 197 and key 198.

Figure 4B:
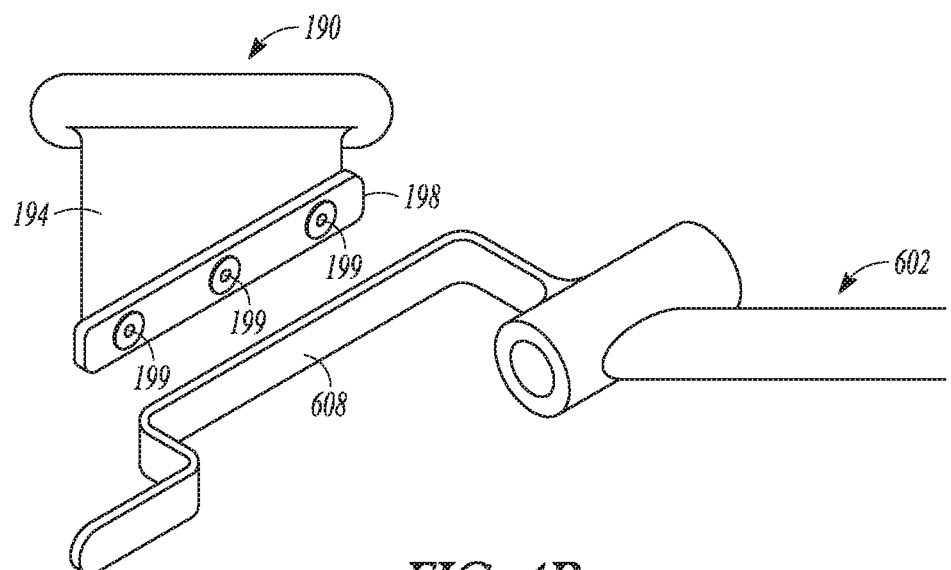
FIG. 4B is a perspective view of the level indicator of FIG. 4A being attached to a drill guide.

FIG. 4B is a perspective view of level indicator 190 of FIG. 4A being attached to drill guide 602 (see FIG. 6B). In one example, key 198 of body 194 is attached to stabilizer 608 using magnets 199. However, as discussed below with respect to FIG. 6B, level indicators described herein can be attached to stabilizer 608, or other portions of drill guide 602, using other suitable arrangements.

Figure 4C:
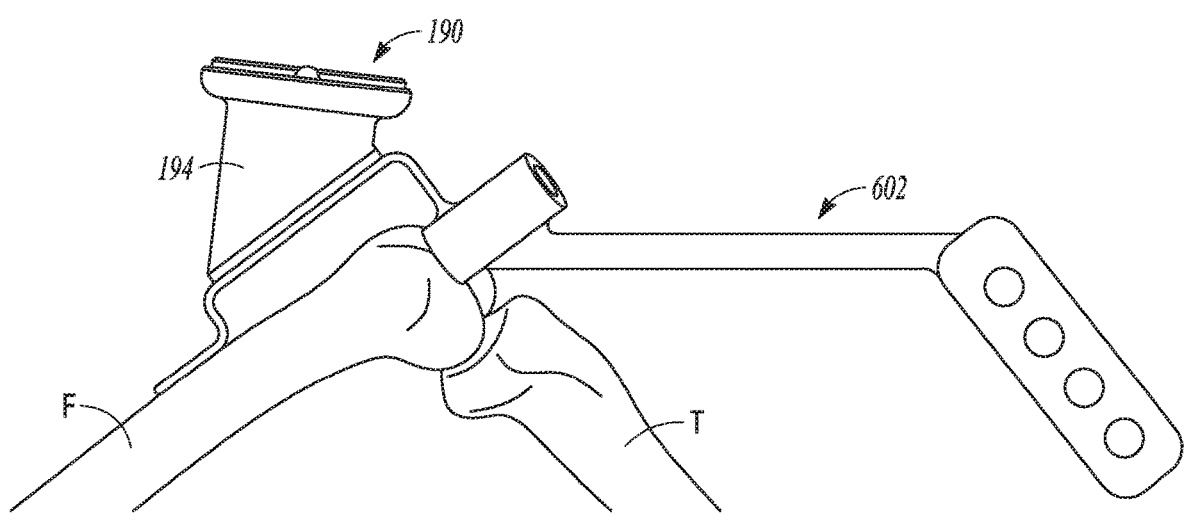
FIG. 4C is a perspective view of the level indicator and drill guide of FIGS. 4A and 4B mated with a femur.

FIG. 4C is a perspective view of level indicator 190 and drill guide 602 of FIGS. 4A and 4B mated with femur F. As discussed below with reference to FIG. 6B, drill guide 602 is used to drill bores within femur F in a desired orientation with the aid of level indicator 190.

Figure 5B:
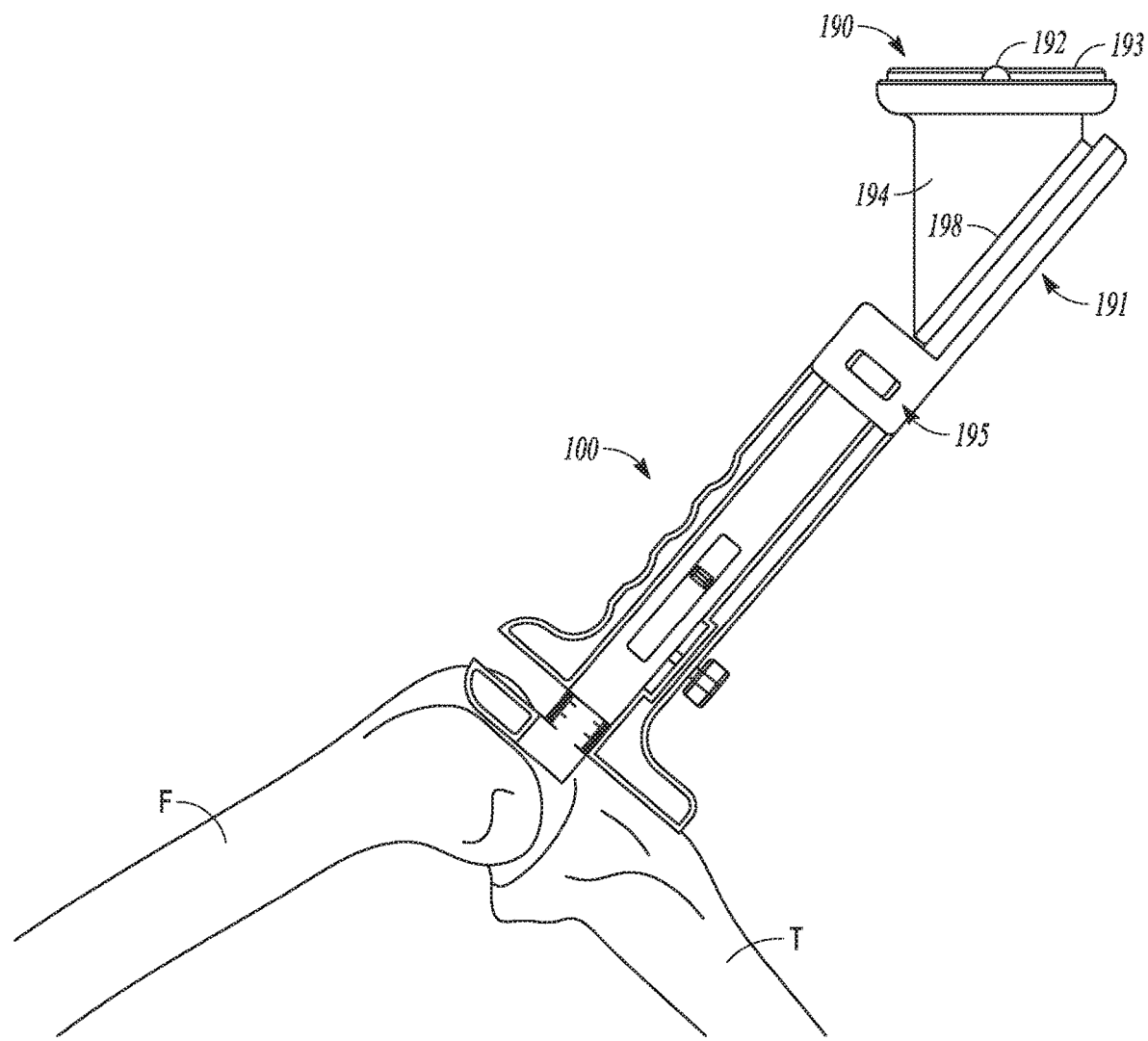
FIG. 5B is another example of the multi-purpose tool of FIG. 3A having a bubble level indicator similar to the one shown in FIG. 4A.

FIG. 5A is a perspective view of another example of multi-purpose tool 200 having separable piece 250 including level device 256—configured as a bubble level indicator—oriented to measure the anterior-posterior (A-P) offset of tibia T from femur F. Tool 200 includes many of the same features of tool 10 of FIG. 1 and tool 100 of FIG. 3A, and such features are denoted with similar reference numerals, but in the two-hundred series. FIG. 5B is another example of multi-purpose tool 100 of FIG. 3A having a bubble level indicator similar to the one shown in FIG. 4A.

FIG. 5A shows a schematic of femur F and tibia T in 90 degrees of flexion. A distance can be measured from anterior location 280 on proximal surface 282 of the tibia T to distal medial condyle 284 of femur F. Separable piece 250 can include level device 256, which in the example of FIG. 5A, comprises bubble 286 disposed in tube 288.

Separable piece 250 can be connected to beam 214 of tool 200 via attachment features 252. For example, beam 214 can be inserted into a slot within separable piece 250 such that internal ends of protrusions 268 are inserted into mating recesses on the exterior of beam 214. Separable piece 250 can be shaped such that surface 264 is disposed along axis $B_1$ at an angle $\theta_2$ of forty-five degrees to axis $A_1$.

Tool 200 may be configured to measure an anterior-posterior (A-P) offset, which is the distance D that tibia T is in front of femur F when axis $A_2$ is disposed ninety degrees to axis $A_3$. In order to measure the A-P offset, femur F and tibia T are disposed at a ninety degree angle to each other. Typically, with the patient resting in the supine position on an operating table, femur F and tibia T are manually moved ninety degrees to each other by the surgeon or staff. In such a position, the A-P offset is readily measurable. Proper measurement of the A-P offset will help ensure the anterior/posterior position of the tibia is restored to its natural, pre-arthritic state.

From the position shown in FIG. 5A, beam 214 can be moved into axial alignment with the major axis $A_2$ of femur F so that surface 239 contacts distal medial condyle 284 of femur F and surface 238 of fixed jaw 220 contacts anterior location 280 of tibia T. In order to help ensure that the A-P offset measurement is taken in the correct position (e.g. that femur F and tibia T are at ninety degrees to each other), tool 200 includes level device 256 that allows the surgeon to correctly position tool 200 by pivoting stationary jaw 220 about anterior tibia 280, in the flexion/extension axis of the knee. If femur F is correctly positioned at forty-five degrees to horizontal, surface 264 will be positioned horizontally and bubble 286 will align between hash marks surrounding the center of tube 288. If bubble 286 is not between the hash marks, tool 200 should be repositioned. Level device 256 also helps ensure that the proper orientation of tool 200 can be repeated when measuring the A-P offset of the implanted replacement knee joint subsequent to the measuring of the A-P offset in the natural knee joint.

Configured as described, level device 256 can be used to determine level in a sagittal plane including femur F, tibia T and tool 200. Alternatively, level device 256, or another level device included with separable piece 250, can be provided to determine level in a transverse plane that is perpendicular to the surface upon which the patient is resting. In addition to bubble levels and roller ball levels, yet other examples of level devices suitable for use with the present multi-purpose tool are laser levels and gyroscopic levels. Additionally, plumb bob levels and accelerometer levels may be used, as are discussed with reference to FIGS. 5C and 5D.

Figure 5C:
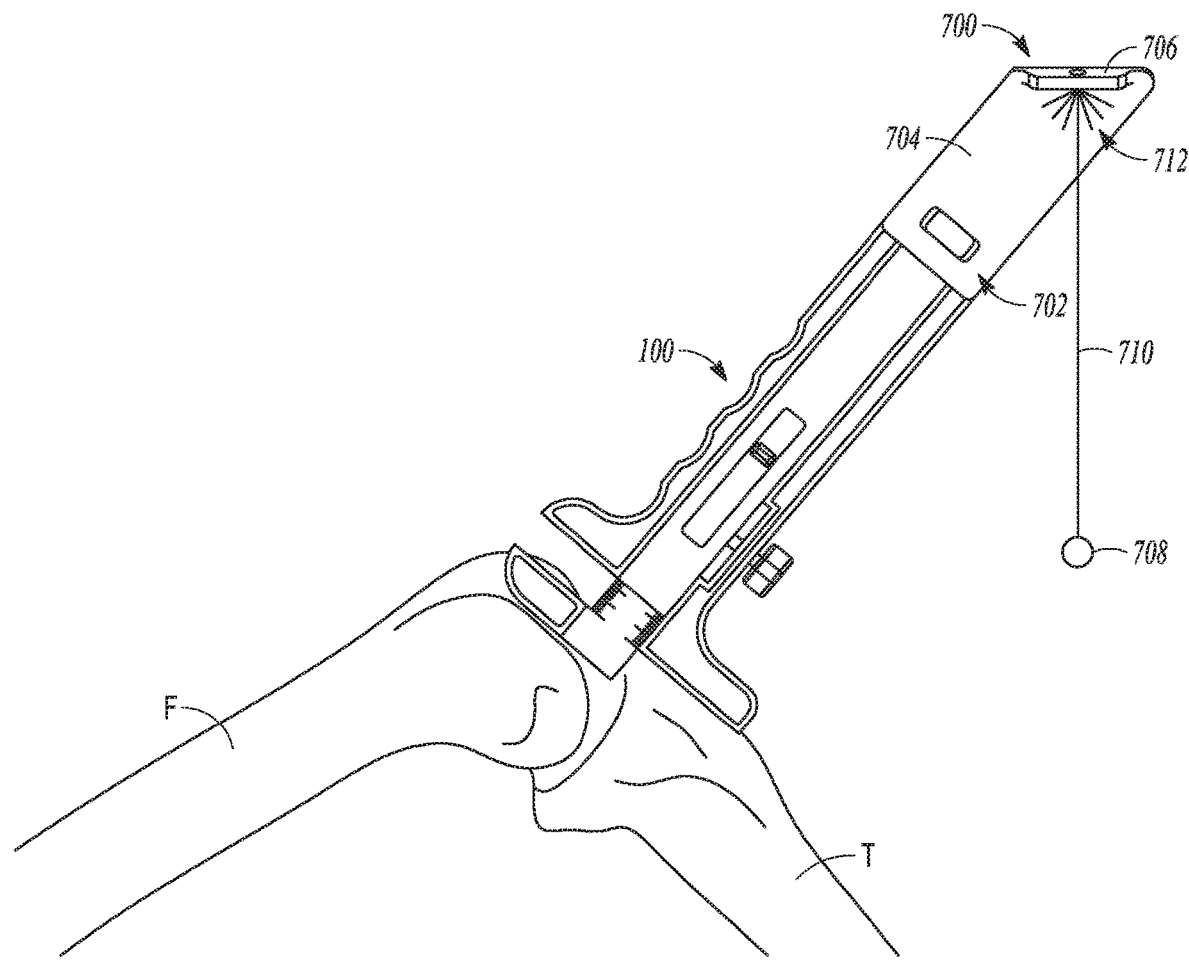
FIG. 5C is another example of the multi-purpose tool of FIG. 3A having a plumb bob level indicator.

FIG. 5C is another example of multi-purpose tool 100 of FIG. 3A having plumb bob level indicator 700. Plumb bob level indicator 700 can be connected to tool 100 using clip 702 on body 704. Body 704 can also include flange 706 from which plumb 708 is suspended via wire 710. Angular indicia marks 712 are provided on body 704 to give an indication of the angular orientation of wire 710 relative to horizontal, or which may be translated to give an indicia of the orientation of femur F.

Figure 5D:
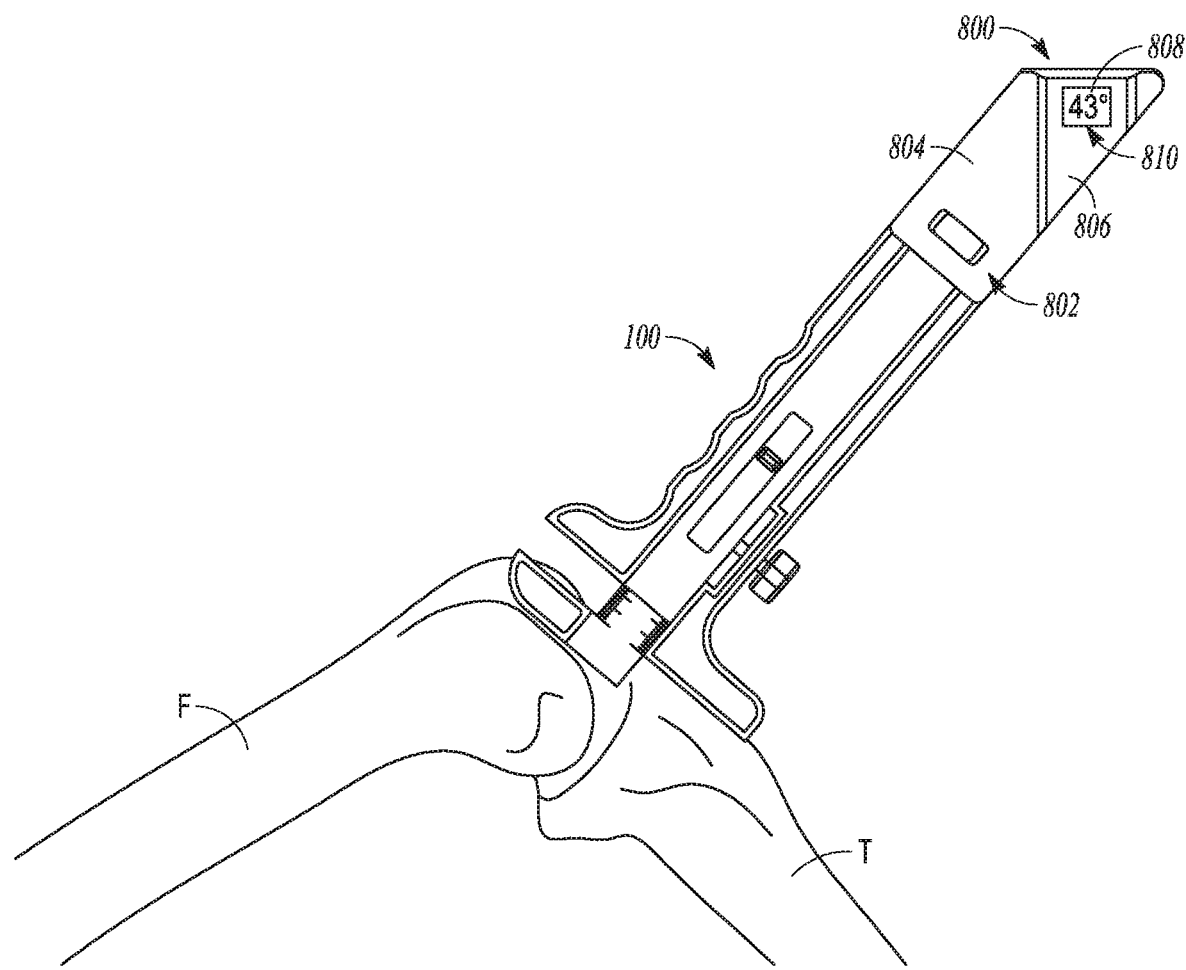
FIG. 5D is another example of the multi-purpose tool of FIG. 3A having an accelerometer-based level indicator.

FIG. 5D is another example of multi-purpose tool 100 of FIG. 3A having accelerometer-based level indicator 800. Accelerometer-based level indicator 800 can be connected to tool 100 using clip 802 on body 804. Body 804 can also include compartment 806 in which may be disposed accelerometer 808 that is configured to operate as an inclinometer. Accelerometer 808 may include digital indicia 810 that give an indication of the angular orientation of femur F to horizontal. Although described with respect to an accelerometer, other types of sensors may be used in level indicators described herein.

Figure 6A:
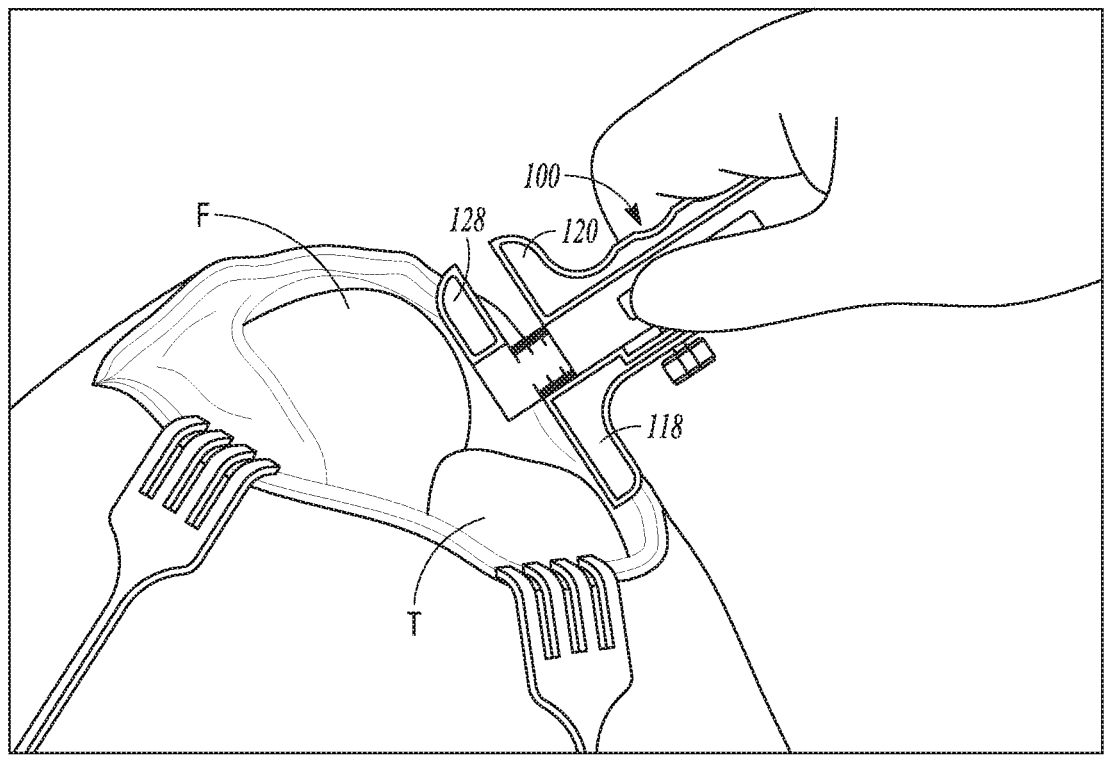
FIG. 6A illustrates one step of a total knee arthroplasty using a multi-purpose tool to measure a natural anterior-posterior offset of the anterior portion of a tibia to the distal end of a femur using a sliding depth gauge.
Figure 6B:
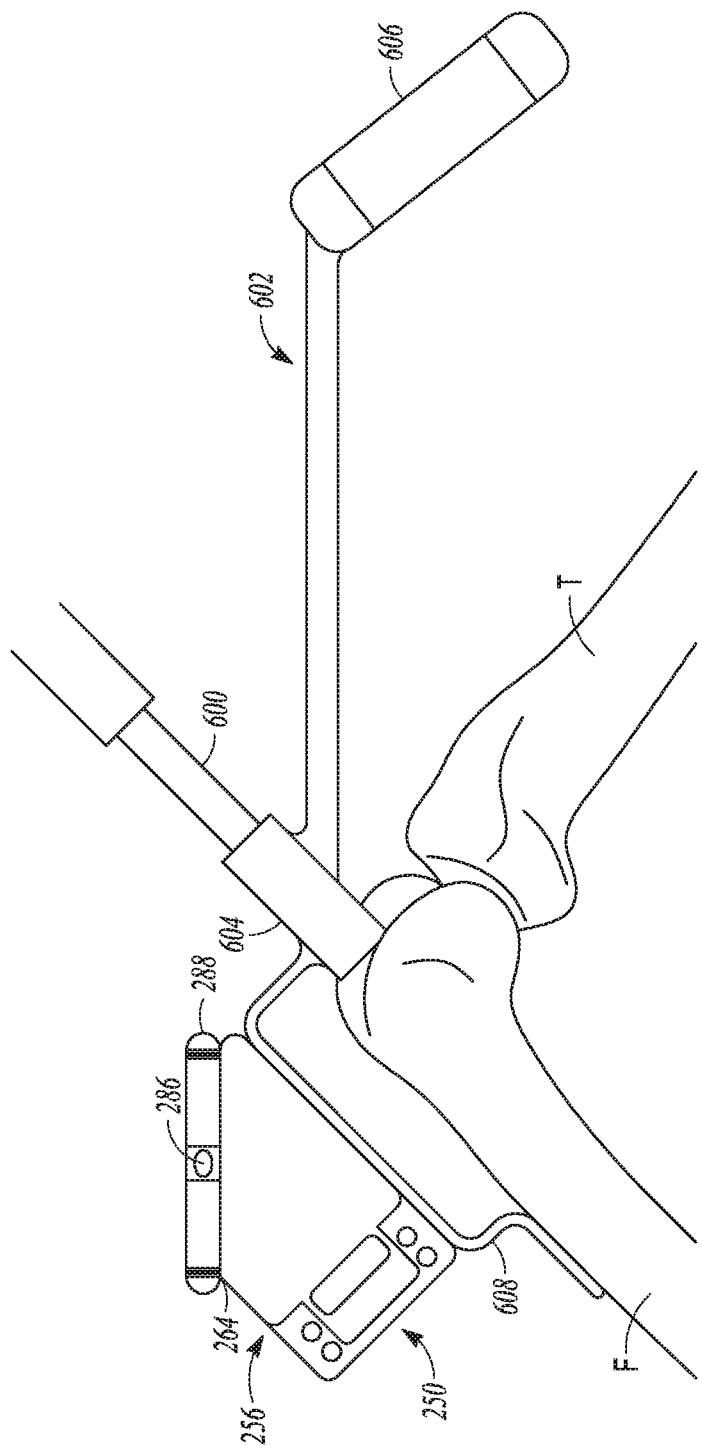
FIG. 6B illustrates another step of a total knee arthroplasty using a multi-purpose tool to indicate alignment of a drill bit with a femur.

FIG. 6A illustrates one step of a total knee arthroplasty (TKA) procedure using multi-purpose tool 100 to measure a natural anterior-posterior (A-P) offset of tibia T from the femur F using a sliding depth gauge formed by fixed jaw 118 and moveable jaw 128. An objective of the kinematically aligned TKA is that a thickness of the femoral component of the knee prosthesis be equal to the sum of the thickness of the bone resection and the thickness of the cartilage wear, accounting also for the thickness of the surgical saw blade used to resect the bone. As such, it can be desirable to accurately measure the thickness of any resections removed from the knee.

The location and extent of wear on the knee of a patient is determined pre-operatively and confirmed after femur F and tibia T of the knee is exposed, as shown in FIG. 6A. X-ray imaging or computed tomography (CT) scans can be used to aid pre-operative evaluation of cartilage loss and to determine the formation of any osteophytes which could alter soft-tissue tension. A medial, subvastus or midvastus approach can be used to expose the distal medial femoral condyle with the knee in ninety degrees of flexion. The A-P offset measurement described above in reference to FIG. 5A can be performed after the knee is exposed and before the distal resections described below are performed. A tool, such as, for example, tool 10 of FIGS. 1 and 2 or tool 100 of FIGS. 3A-3E, etc., can also be used for measuring the distance D when the knee is in ninety degree flexion. A determination of the wear on the femoral condyle can be conducted and recorded.

The obtained measurement can represent the natural A-P offset of the patient. If the cartilage is worn on medial condyle 284, then two millimeters can be subtracted from the distance D to account for the wear. In an example, if the measured distance is 15 mm and the medial condyle is worn, the natural offset is determined to be 13 mm. The natural offset can be recorded for later reference in the surgical technique. For example, the offset can be matched during trial reduction by adjusting the thickness of the tibial liner or adjusting the posterior slope of the tibial bone resection.

FIG. 6B illustrates another step of a TKA procedure using multi-purpose tool 100 to indicate alignment of drill bit 600 with femur F. Drill bit 600 can be inserted into drill guide 602, which includes bit sleeve 604, handle 606 and stabilizer 608. Guide 602 can be placed on femur F in a position to align bit sleeve 604 with a position for an intramedullary rod that can be inserted into a canal of femur F. The rod can provide a marker for performing other steps of the procedure, such as resecting femur F using a shim block assembly, resection tower and cut guide, as is discussed in the aforementioned provisional application No. 62/031,572.

The bore for the intramedullary rod can be located in the femoral intramedullary (IM) canal. It can be desirable that the drill bore for the intramedullary rod be drilled straight into femur F so subsequent drilling and cutting operations can be accurately performed. In other words, the intramedullary bore can extend perpendicular to the distal articular surface of femur F.

A level device, such as level device 256 comprising a bubble level indicator, can be used to facilitate drill bit 600 being inserted into femur F parallel to the long axis of femur F, or in some other desirable orientation. Level device 256 can be removed from tool 200 (FIG. 6A), or any tool to which it can be attached, and joined to stabilizer 608. In one example, level device 256 can be attached using reusable mechanisms, such as a slot and groove, wherein the body of level device 256 can include an edge having a dovetail shape and stabilizer 608 can include a correspondingly shaped slot. In other examples, level device 256 can be secured to stabilizer 608 with other means, such as hook and loop fastener material, a threaded engagement, a magnetic interaction, sockets or the like.

As with the performing of the A-P offset measurements described above with reference to FIG. 5A, surface 264 can be disposed at an angle relative to separable piece 250 such that when femur F is disposed at forty-five degrees to horizontal, tube 288 will be level so that bubble 286 aligns between centered hash marks on tube 288. This helps ensure that bit sleeve 604 directs drill bit 600 straight into femur F (e.g. along axis $A_2$ of femur F in FIG. 5A).

After the drilling is performed, a shim block that includes the appropriately selected shim based on the cartilage condition of both the medial and lateral distal femoral condyles can be attached to femur F. The shim block assembly can set a location for where the distal resections are made on femur F using the cut guide to control the thickness of the bone resections. A saw blade or other cutting tool can then be inserted through a slot in the cut guide to perform the distal resections of the medial and lateral condyles.

Figure 6C:
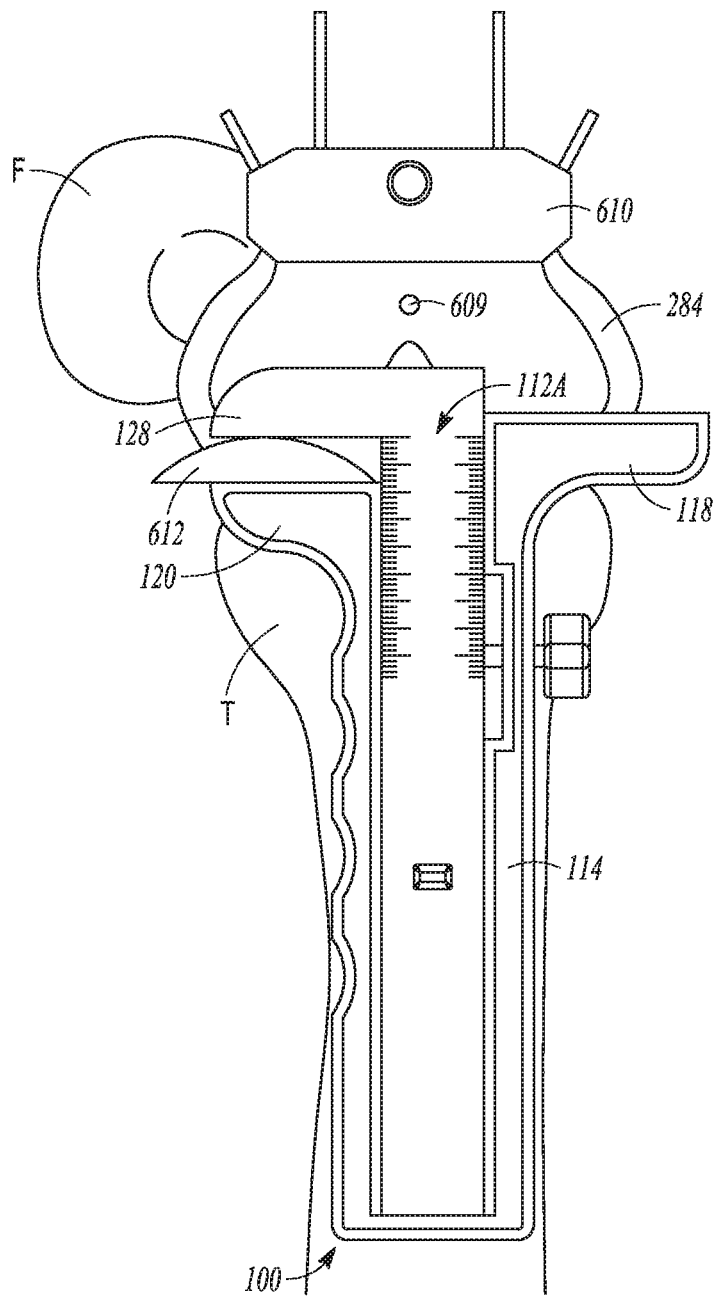
FIG. 6C illustrates an additional step of a total knee arthroplasty using a multi-purpose tool to measure a thickness of distal femoral resection using a sliding thickness gauge.

FIG. 6C illustrates an additional step of a TKA procedure using multi-purpose tool 100 to measure a thickness of a distal femoral resection using a sliding thickness gauge formed by moveable jaw 128 and fixed jaw 118. The distal resections are described below as being performed with use of the intramedullary rod, discussed with reference to FIG. 6B, which can be inserted into drill bore 609. It is recognized that an extramedullary alignment technique can also be used. Cut guide 610 is shown attached to femur F with distal medial condyle 284 (FIG. 5A) and the distal lateral condyle resected. Resected bone 612 (e.g. distal medial femoral resection 290 of FIG. 5A) from distal medial condyle 284 is shown positioned between fixed jaw 120 and moveable jaw 128 of tool 100. Fixed jaw 120 and moveable jaw 128 function as a thickness gauge, or caliper, that provides an indication of the measured thickness of resected bone 612 using scale 112A. Assuming the thicknesses of the distal condyles of the prosthetic femoral component are 9 millimeters, the resection of a worn condyle should measure approximately 6 mm thick and an unworn condyle should be approximately 8 mm thick (compensating for approximately 1 mm blade thickness).

After each of the distal medial and lateral condyles are resected, a thickness of each of the two resected bones can be measured to confirm that the target medial and lateral resection thicknesses were obtained. (Alternatively, the first resection can be performed and measured; and then the second resection can be performed and measured.) FIG. 6C shows tool 100 being used, but any tool described herein can be used.

Figure 6D:
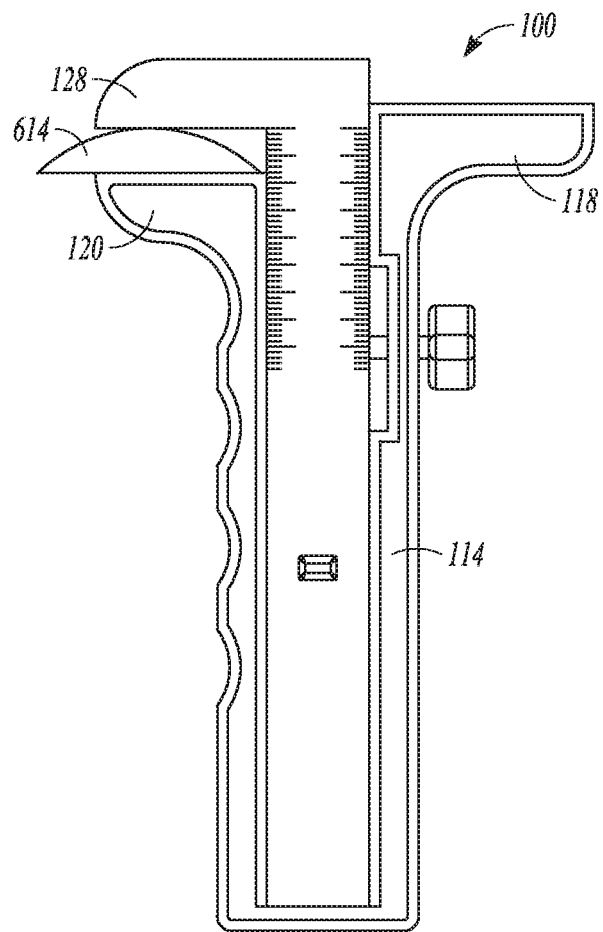
FIG. 6D illustrates a further step of a total knee arthroplasty using a multi-purpose tool to measure a thickness of a posterior femoral resection using a sliding thickness gauge.

FIG. 6D illustrates a further step of a TKA procedure using multi-purpose tool 100 to measure a thickness of resected bone 614 (e.g. posterior medial femoral resection 292 of FIG. 5A) resulting from a posterior femoral resection using a sliding thickness gauge, or caliper, formed by fixed jaw 120 and moveable jaw 128. Posterior femoral resectioning can be performed using a cut block inserted into holes drilled into the distal end of femur F. A size of the cut block can be selected to match the size of the femur F. The cut block provides a guide for removing bone from the posterior portion of femur F at the desired thickness. After each of the posterior medial and lateral condyles are resected, a thickness of each of the two resected bones can be measured to confirm that the target medial and lateral resection thicknesses were obtained. FIG. 6D shows tool 100 being used, but any tool described herein can be used. The thickness of the posterior medial and lateral femoral resections should each be 8 mm (compensating for approximately 1 mm blade thickness).

Figure 6E:
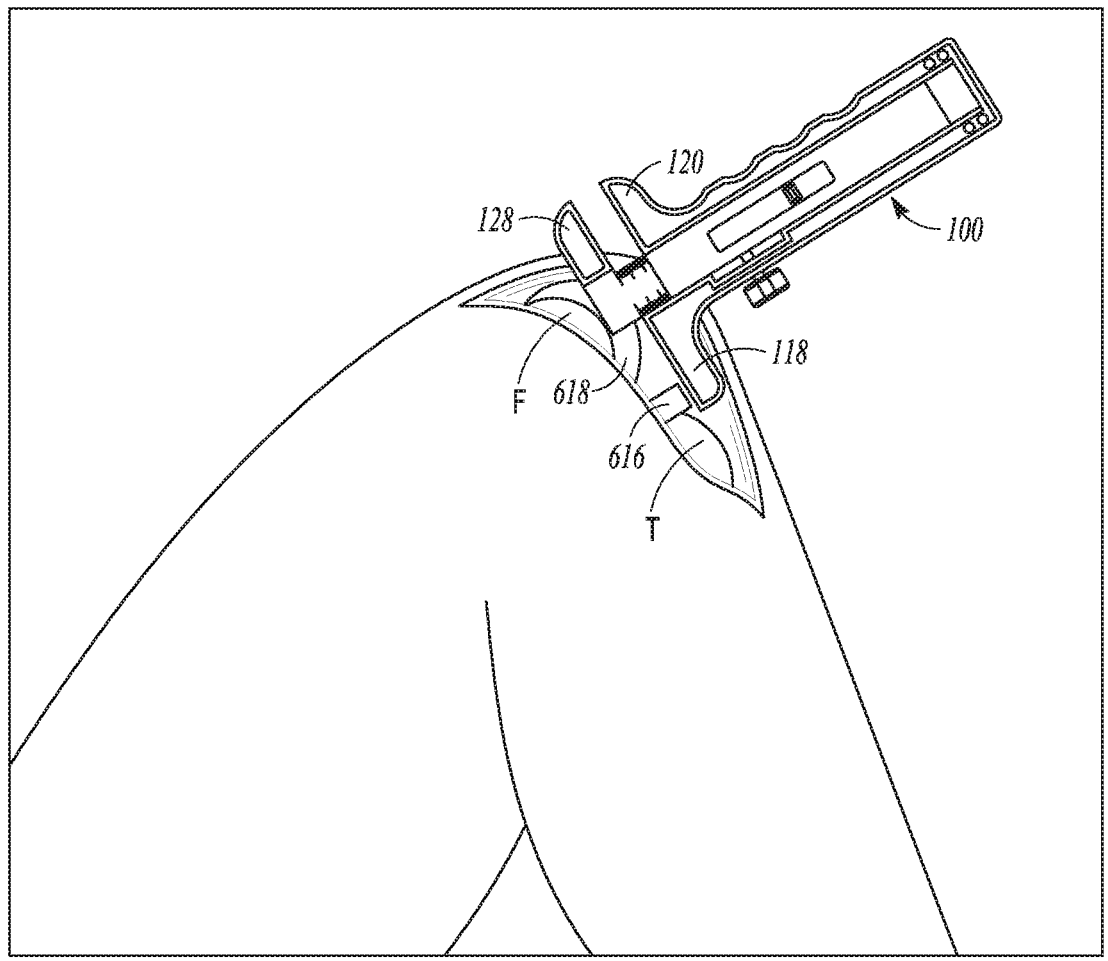
FIG. 6E illustrates yet another step of a total knee arthroplasty using a multi-purpose tool to measure the anterior-posterior offset of the anterior portion of an implanted prosthetic tibia to the distal surface of an implanted prosthetic femur using a sliding depth gauge.

FIG. 6E illustrates yet another step of a TKA procedure using multi-purpose tool 100 to measure an anterior-posterior offset of tibia T from the femur F after using a sliding depth gauge, or caliper, formed by moveable jaw 128 and fixed jaw 120. Subsequent to resectioning of femur F, tibia I can be appropriately resectioned. Then, tibial baseplate and liner 616 and femoral component 618 can be installed on tibia T and femur F. Tool 100 can then be used to measure the A-P offset of implanted tibial liner 616 from the implanted femoral component 618 resulting from the TKA procedure. The implant A-P offset should correspond to the natural A-P offset measured as described with reference to FIG. 6A. If the measured A-P offsets are not within an acceptable tolerance band of each other, corrective action can be taken, such as performing additional resectioning of tibia T, or increasing the thickness of tibial liner 616.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A multi-purpose measurement tool comprising:
    an elongate beam having a longitudinal axis extending from a first end to a second end, the elongate beam comprising:
    a first fixed jaw extending from the beam at the first end and extending from a first side of the beam perpendicular with respect to the longitudinal axis, wherein the first jaw is configured to abut a proximal surface of a tibia;
    a second fixed jaw extending from the beam from a second side transverse with respect to the longitudinal axis such that the second jaw is opposite the first jaw with respect to the longitudinal axis and spaced axially along the longitudinal axis from the first end; and
    a track extending across the elongate beam along the longitudinal axis through the first end;
    a slide having a first end extending from the track and a second end extending into the track, the slide having a moveable jaw extending from the slide on the second side with respect to the longitudinal axis so as to be opposite the first fixed jaw with respect to the longitudinal axis, wherein the moveable jaw is configured to abut a distal surface of a femur when the first end of the slide extends from the track, wherein the slide has a front face and a back face that are each transverse to the first side and the second side of the beam, and wherein the front face has a first indicia configured as a depth gauge to measure an anterior-posterior offset between a proximal tibia and the femur that comprises a first distance between the first fixed jaw and the moveable jaw when the first fixed jaw and the moveable jaw are abutting the tibia and femur, respectively, and the back face has a second indicia configured as a thickness gauge to measure a thickness of a distal femoral resection of the femur that comprises a second distance between the second fixed jaw and the moveable jaw when the moveable jaw is abutting the femur; and
    a level indicator mounted to the beam and configured to indicate a level reading when the beam is disposed at forty-five degrees from horizontal.

2. The multi-purpose measurement tool of claim 1, wherein the elongate beam comprises:
    a plate portion;
    a first rail extending from the plate portion to define a first side of the track and a portion of the first fixed jaw; and
    a second rail extending from the plate portion to define a second side of the track and a portion of the second fixed jaw;
    wherein the slide with the moveable jaw slides in the track defined by the first rail and second rail of the plate portion; and
    wherein the plate portion, the first rail and the second rail define an outer perimeter of the elongate beam.

3. The multi-purpose measurement tool of claim 2, wherein the plate portion is transparent.

4. The multi-purpose measurement tool of claim 1, wherein the second fixed jaw is spaced from the first end a distance equal to a width of the moveable jaw.

5. The multi-purpose measurement tool of claim 1, wherein the level indicator is positioned at the second end of the beam.

6. The multi-purpose measurement tool of claim 5, wherein the level indicator comprises a bubble.

7. The multi-purpose measurement tool of claim 5, wherein the level indicator is selected from the group consisting of a roller ball, a plumb bob, or an accelerometer-based level indicator.

8. The multi-purpose measurement tool of claim 5, further comprising an attachment including the level indicator.

9. The multi-purpose measurement tool of claim 8, wherein the second end of the elongate beam is configured to receive the attachment and includes a connection to immobilize the attachment.

10. The multi-purpose measurement tool of claim 1, wherein the slide includes a thumb grip.

11. The multi-purpose measurement tool of claim 1, wherein the first side of the elongate beam from which the first fixed jaw extends includes a fixation device for immobilizing the slide relative to the elongate beam.

12. The multi-purpose measurement tool of claim 11, wherein the second side of the elongate beam includes ergonomic grips.

13. A multi-purpose measurement tool for use in a total knee arthroplasty to measure an anterior-posterior offset of a tibia from a femur, comprising:
    an elongate beam having a longitudinal axis extending from a first end to a second end, the elongate beam comprising:
    a first fixed jaw extending from the beam at the first end and extending from a first side of the beam perpendicular with respect to the longitudinal axis, wherein the first jaw in configured to abut a proximal surface of the tibia;
    a second fixed jaw extending from the beam from a second side transverse with respect to the longitudinal axis such that the second jaw is laterally opposite the first jaw and spaced axially from the first end along the longitudinal axis; and
    a track extending across the elongate beam along the longitudinal axis through the first end;
    a slide having at least a portion moveable along the track, the slide having a moveable jaw extending from the slide on the second side with respect to the longitudinal axis so as to be laterally opposite the first fixed jaw with respect to the longitudinal axis, wherein the moveable jaw is configured to abut a distal surface of the femur when a first end of the slide extends from the track, wherein the slide has a first face and a second face that are each transverse to the first side and the second side of the beam, and wherein the first face has a first indicia configured as a depth gauge to measure the anterior-posterior offset between the tibia and femur that comprises a first distance between the first fixed jaw and the moveable jaw when the first fixed jaw and the moveable jaw are abutting the tibia and femur, respectively, and the second face has a second indicia configured as a thickness gauge to measure a thickness of a distal femoral resection of the femur that comprises a second distance between the second fixed jaw and the moveable jaw when the moveable jaw is abutting the femur; and a level indicator mounted to the second end of the elongate beam, wherein the level indicator is configured to display an orientation of the femur relative to a horizontal so that a proper alignment of the femur for measurement of the anterior-posterior offset of the tibia from the femur is achieved.

14. The multi-purpose measurement tool of claim 13, wherein the elongate beam comprises:
   a plate portion;
   a first rail extending from the plate portion to define a first side of the track and a portion of the first fixed jaw; and
   a second rail extending from the plate portion to define a second side of the track and a portion of the second fixed jaw;
   wherein the slide with the moveable jaw slides in the track defined by the first rail and second rail of the plate portion; and
   wherein the plate portion, the first rail and the second rail define an outer perimeter of the elongate beam.

15. The multi-purpose measurement tool of claim 13, wherein the track extends along the longitudinal axis of the beam and the jaws extend transverse to the longitudinal axis.

16. The multi-purpose measurement tool of claim 13, wherein the plate portion is transparent.

17. The multi-purpose measurement tool of claim 13, wherein the level indicator comprises one of a bubble, a roller ball, a plumb bob, or an accelerometer-based level indicator.

18. The multi-purpose measurement tool of claim 13, wherein the level indicator indicates a level reading when the elongate beam is disposed at forty-five degrees from the horizontal.

19. The multi-purpose measurement tool of claim 13, further comprising an attachment including the level indicator.

* * * * *

UNITED STATES PATENT AND TRADEMARK OFFICE
CERTIFICATE OF CORRECTION

| | |
|---|---|
| PATENT NO. | : 10,582,982 B2 |
| APPLICATION NO. | : 15/073167 |
| DATED | : March 10, 2020 |
| INVENTOR(S) | : Fisher et al. |

It is certified that error appears in the above-identified patent and that said Letters Patent is hereby corrected as shown below:

In the Claims

In Column 14, Line 38, in Claim 13, delete "in" and insert --is-- therefor

Signed and Sealed this
Third Day of September, 2024

Katherine Kelly Vidal
*Director of the United States Patent and Trademark Office*